US011307437B2

(12) United States Patent
Parandian et al.

(10) Patent No.: US 11,307,437 B2
(45) Date of Patent: Apr. 19, 2022

(54) METHOD OF DESIGNING AND PLACING A LENS WITHIN A SPECTACLES FRAME

(71) Applicants: MATERIALISE N.V., Leuven (BE); HOYA CORP., Tokyo (JP)

(72) Inventors: Alireza Parandian, Leuven (BE); Tom Cluckers, Leuven (BE); Jan Maes, Leuven (BE); Takashi Hatanaka, Tokyo (JP)

(73) Assignee: Materialise NV, Leuven (BE)

( * ) Notice: Subject to any disclaimer, the term of this patent is extended or adjusted under 35 U.S.C. 154(b) by 724 days.

(21) Appl. No.: 16/300,027

(22) PCT Filed: May 10, 2017

(86) PCT No.: PCT/US2017/031912
§ 371 (c)(1),
(2) Date: Nov. 8, 2018

(87) PCT Pub. No.: WO2017/196948
PCT Pub. Date: Nov. 16, 2017

(65) Prior Publication Data
US 2019/0146243 A1 May 16, 2019

Related U.S. Application Data

(60) Provisional application No. 62/398,379, filed on Sep. 22, 2016, provisional application No. 62/382,598, filed on Sep. 1, 2016, provisional application No. 62/334,128, filed on May 10, 2016.

(51) Int. Cl.
*G02C 7/02* (2006.01)
*G02C 13/00* (2006.01)
*G16H 20/40* (2018.01)
*G06Q 30/06* (2012.01)
*G02C 7/06* (2006.01)

(52) U.S. Cl.
CPC ........... *G02C 7/027* (2013.01); *G02C 13/005* (2013.01); *G06Q 30/0603* (2013.01); *G06Q 30/0621* (2013.01); *G06Q 30/0633* (2013.01); *G16H 20/40* (2018.01); *G02C 7/06* (2013.01)

(58) Field of Classification Search
CPC ........ G02C 7/027; G02C 13/005; G02C 7/06; G16H 20/40; G06Q 30/0603; G06Q 30/0621; G06Q 30/0633
See application file for complete search history.

(56) References Cited

U.S. PATENT DOCUMENTS

| | | |
|---|---|---|
| 6,533,418 B1 | 3/2003 | Izumitani et al. |
| 2003/0123026 A1 | 7/2003 | Abitbol et al. |
| 2010/0296055 A1* | 11/2010 | Esser .................... G02C 7/061 351/204 |
| 2015/0055085 A1 | 2/2015 | Fonte et al. |

FOREIGN PATENT DOCUMENTS

| | | |
|---|---|---|
| WO | 01/88654 A2 | 11/2001 |
| WO | 2014195471 A1 | 12/2014 |

* cited by examiner

*Primary Examiner* — James C. Jones
(74) *Attorney, Agent, or Firm* — Patterson + Sheridan, LLP

(57) ABSTRACT

Described herein are methods and systems for customizing and personalizing eyewear. The methods and system consider optimal parameters for each wearer's personal visual situation and configures frames around them.

20 Claims, 8 Drawing Sheets

Lens Data Management

METHOD OF DESIGNING AND PLACING A LENS WITHIN A SPECTACLES FRAME

CROSS-REFERENCE TO RELATED APPLICATION & PRIORITY CLAIM

The present application claims the benefit of U.S. Provisional Patent Application Ser. No. 62/334,128, filed May 10, 2016, U.S. Provisional Patent Application Ser. No. 62/382,598, filed Sep. 1, 2016, and U.S. Provisional Patent Application Ser. No. 62/398,379, filed Sep. 22, 2016, all of which are hereby expressly incorporated by reference in their entirety.

FIELD OF THE INVENTION

This application relates to custom eyewear. More particularly, this application relates to eyewear frames that are designed and configured around lenses.

BACKGROUND

Traditionally, eyewear design is frame-centric. Designers create frames, users select a frame, and then opticians adapt lenses to the selected frame. This approach offers tremendous design freedom, which is evidenced by the diverse range of styles, sizes, shapes, materials, and colors available for frames.

While comfort and appearance are well-served by current frame technologies, visual experience is not. For correction of vision, which is the primary reason for using eyewear, optical performance depends on lenses more than on frames. In order for a lens to correct the light refractive errors in eyes that lead to conditions such as near-sightedness, far-sightedness, astigmatism, and presbyopia, the lens optics must be individually prescribed for each eye and placed in the correct position and orientation in front of the eye. When lenses are not properly fitted, wearers suffer from visual discomfort, eyestrain, headaches, and poor vision. As one example, the position of the lenses should account for the pantoscopic angle, which is the angle between the optical axis of the lens and the visual axis of the eye in its primary position. The optical center of the lenses is typically lowered by 1 mm for each 2 degrees of pantoscopic angle, otherwise the wearer is likely to experience lens aberrations induced by changes in sphere and cylinder powers outside of the optical center. For multifocal or progressive lenses, the position of the lens in relation to the eye is even more critical.

In the current environment, where frames are selected first and lenses are made to fit the frame, the frame design can impose constraints which result in lenses that are not optimally positioned or oriented in front of the wearer's eyes. In some cases, a wearer can tolerate or adapt to the optics of a lens that is not correctly positioned. In other cases, the negative effects of a poorly-positioned lens cannot be overcome, and the wearer will first suffer from the effects and then try many solutions to solve the problem. The consequences for these wearers are physical discomfort, time and money spent in looking for solutions, and too often, the challenge of selecting a different frame that better accommodates the wearer's needs. There remains a need in the art for improving both the fit and the visual experience for wearers of eyewear.

SUMMARY OF INVENTION

One aspect of the present disclosure relates to a computer-implemented method for constructing custom eyewear, comprising receiving wearer information related to anatomy and lifestyle of a wearer of the custom eyewear; calculating, based at least in part on the anatomy and lifestyle of the wearer, values for lens parameters, wherein the lens parameters set a lens position that is optimized for the wearer; obtaining a scanned image showing morphology of an anatomical part of the wearer; selecting a frame from a digital catalog; and modifying the frame to accommodate the values for the lens parameters and the scanned image, thereby building the frame and constructing custom eyewear.

Values for the lens parameters may be optimized for one or more of prescription data, previous glasses, lens type, and pupillary distance (PD), and the scanned image.

In some embodiments, the prescription data comprises measurements for bifocal, trifocal, or multifocal lenses.

In certain embodiments, the lens position set by the lens parameters includes corrective features in a first region of the lens and includes non-essential features in a second region of the lens.

Lens parameters may comprise at least one of lens offset (x & z), pantoscopic angle (PA), corneal vertex distance (CVD), lens face form angle (LFFA), minimal eye point height (EPH), minimal B-size, minimal distance to upper, and minimum corridor length. The values for the lens parameters may be selected from an ideal value and a range of tolerated values for the lens parameters.

In some embodiments, selecting the frame comprises choosing a frame that accommodates the values for the lens parameters. Modifying the frame may comprise modifying values for one or more frame parameters.

Frame parameters may comprise a frame model ID, OMA data, HBox, VBox, incline, frame face form angle (FFFA), parametric model, color options, frame material, groove type, and bevel type.

In certain embodiments, the methods described herein further comprise making a lens calculation based on the one or more frame parameters, wherein the lens calculation approximates the optimal lens for a frame having the frame parameters.

The methods may further comprise performing a lens reconstruction to create 3D lens shape based on the optimal lens from the lens calculation.

In some embodiments, the methods further comprise performing an auto fitting of the 3D lens shape, selected frame, and scanned image showing morphology of an anatomical part of the wearer.

An output of the auto fitting may comprise lens parameters selected from one or more of PA, CVD, LFFA, EPH, and distance to upper rim and frame parameters selected from DBL, HBox, VBox, FFFA, inclination angle, and temple length.

In certain embodiments, lens materials/codes may be added to the frame parameters for frame fitting. For example, the methods may further comprise making a change to a different lens material and performing at least one further iteration of lens calculation, frame optimization, and/or auto-fitting.

A further step may comprise making a change to frame parameters and optionally performing at least one further iteration of auto-fitting.

In some embodiments, a final lens calculation is performed based on final calculated lens parameters and frame parameters.

In certain embodiments, a final check for optimization of lens parameters may be performed.

Lens customization may be performed via a customization web service.

In some embodiments, the lens customization comprises selecting at least one of a frame design, material, treatment, and color; selecting at least one of a lens coating, tint, photo, polarization, filter; and ordering the custom eyewear.

Another aspect of the present disclosure relates to a computer program configured to perform the methods described herein. A further aspect of the present disclosure relates to a computer-readable medium comprising computer-executable instructions, which, when executed by a processor, cause the processor to perform the methods described herein. Yet another aspect of the present disclosure relates to an eyewear product customized according to the methods described herein.

DETAILED DESCRIPTION

Figure 1:
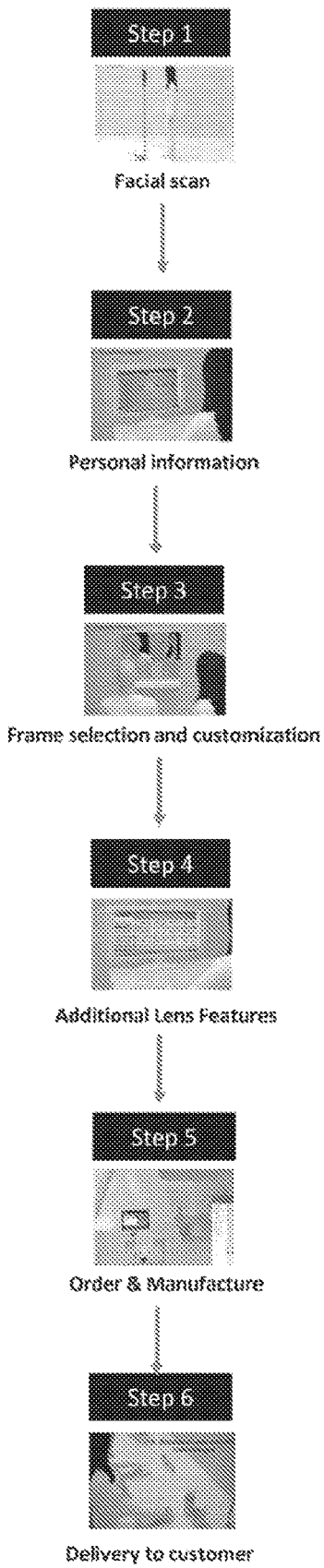
FIG. 1 illustrates example operations for designing customized eyewear, according to certain aspects.

Currently, frames are selected and lenses are fitted to the frames, often to the detriment of the wearer's visual experience. The present inventors recognized that it would be advantageous if a corrective lens could be ensured to properly fit the wearer and if frames could support rather than constrain the proper position of the lenses. Accordingly, disclosed herein are systems and methods for designing and building eyewear frames around lenses. In some embodiments, the systems and methods differ from the traditional approach to eyewear construction, by starting with lens parameters that are optimized for a wearer, and then designing and building frames which accommodate the lenses. In some embodiments, frames may be built using additive manufacturing (AM) techniques. For example, software that is optimized for designing, custom-fitting, and adjusting eyewear may be used to design the frames, and AM processes for production may be used to build the frames. In some embodiments, the AM techniques discussed herein allow for customizing eyewear to the wearer's optical lens requirements. The lens-centric and vision-centric approaches to eyewear design discussed herein may produce custom eyewear that not only fits correctly but also enhances the wearer's visual experience.

Fitting ophthalmic lenses into given eyewear frames, based on frame data as measured before, is the conventional way of assembling eyeglasses. Also, several methods have been proposed to modify or optimize frame data in this process. However, a direct data flow from lens to frame optimization has not been described, nor how it will be performed.

One aspect relates to a calculating system, for an ophthalmic lens and frame, including providing data and deformability data of the frame, the wearer and lens data. Some methods modify ophthalmic frame shape data, by measuring the space of a rim of the frame, determining principle axes of inertia of shape and calculating new rim frame data. Further aspects include methods to optimize frame contour, involving a providing and contour defining step. In addition, corridor length in a lens may be selected from the prepared corridor length variation for the progressive lens, according to a user's life style information and that of basic design for the progressive lens, if a basic design variation, prepared according to user's life style information, can be applied for them. However, corridor length and basic design selection may be limited by frame parameters, which have been measured before.

Eyewear frames are available in a broad range of colors, patterns, styles, shapes, fits, and materials, any of which can be adapted to suit a wearer's preferences. Opticians make general recommendations based on the shape of the wearer's facial features, face shape, face size, etc. For example, an optician may advise a person with an oblong face and large nose to try an eyewear frame that adds width to the face, with temples in contrasting colors or decorative elements at the temples, and a low bridge that would balance the proportions of the features. The most common way to select frames is to try on a variety of models available at the optician's shop.

In some aspects, a wearer's search for suitable frames can be enhanced by the use of virtual fitting systems in which an image of an eyewear frame is superimposed on a scanned image of a wearer's face or head. In some systems, 2D images are used, such as, images of the left and right side of the wearer's face. In some aspects, using 2D images may give a wearer only an approximation of what the eyewear frame looks like on the wearer, as details may be distorted or omitted when 3D shapes, particularly curved shapes like faces and frames, are flattened into 2D images. Accordingly, in some aspects, 3D scanners or algorithms that generate 3D renderings of faces and frames may be used for preparing a virtual fitting. In some aspects, a 3D image based virtual fitting system may extract facial features in order to generate 3D face models with real dimensions, which are then displayed for virtual fitting of eyewear. In another example, a virtual try-on system includes an image processing system and 3D image generator combined with a frame fitter and lens fitter so the frame can be fitted and the lenses can be cut to the specifications of the frame. Similarly, a method for receiving and processing data related to dimensions of a wearer's head, starts with an eyewear design, and uses the data about the wearer's head to create a wearer-specific design for eyewear. Another system generates a 3D model of a wearer's face based on simple images, even using images captured from cameras on handheld devices, and combines this data with a computer that configures eyewear models, displays the model over the wearer's face, and allows customization of the model. The computer can additionally communicate information about the customized eyewear model to a manufacturer.

In some aspects, additive manufacturing (AM) capabilities may be used in combination with the imaging and customization systems. For example, PCT/EP2015/059509 (Materialise N.V.) describes objects including eyewear frames that are customized by fitting a representation of the objects to images of scanned body parts (the head, face, ears of the wearer) and adjusting the objects to fit the body parts precisely. To facilitate production of the object by additive manufacturing, the object is represented and adjusted in a format that is readily printable on a 3D printer.

A link to 3D printing is also found in examples where a customer has his or her face scanned (for example, using a 3D scanner) in a multi-function combination system, for example in an optician's shop. The customer then enters individual requirements and requests, receives images of sample designs which are fitted to the scan of the customer's face, selects a frame, and has it 3D printed on the spot. Finally, methods for customizing eyewear may be based on features in a wearer's face and the information may be sent to a 3D printer in order to manufacture the eyewear.

While some of the aforementioned methods may facilitate the frame selection process, such methods do not properly account for the lenses of the eyewear. Rather, in such methods, the frame is selected and fitted, and the lens is configured to fit the already selected and fitted frames, thereby limiting how the lenses can be fit and positioned in the frames. For example, systems for simulating eyeglasses fitting may be based on lens selection, lens prescription data, lens material data, and lens optical design data, but the lens data is used to determine the shape and appearance of the lens when it is mounted in a pre-selected eyeglasses frame. Some methods use a process to automatically determine the correct geometric parameters for a wearer's lens, but the process depends on a data set that represents a wearer and an already selected eyeglasses frame. Accordingly, the inventors have developed methods and systems for constructing custom eyewear that start with lens parameters and an image of the wearer, and then determine suitable frame parameters based on the lens parameters and image of the wearer.

Scanned Image

In some aspects, custom eyewear is designed and built based on the unique anatomy of the individual who will wear the eyewear. This individual may be referred to herein as the "wearer", "user", "individual", or "customer." In a computer-based system for selecting eyewear, a computing device may generate a realistic digital representation (e.g., digital images) of the wearer by imaging the wearer utilizing an image capture device. For example, digital images of the wearer may be generated by one or more image capture devices, such as, cameras, light sensors, or scanners. Scanners may be optical scanners, infrared scanners, laser scanners, 3D scanners, or medical scanners such as X-ray machines or CT scanners. In some aspects, a computing device determines dimensions of the wearer based on the wearer's image, for example, by using reference objects whose dimensions are known, or by using scale bars or rulers. In some embodiments, digital images may be 3D images, such as those obtained with a 3D scanner. In some embodiments, a computing device may combine two or more 2D digital images to generate a 3D image.

The digital representation of the wearer may include anatomical parts of a wearer. Accordingly, wearer information related to the anatomy of a wearer may be a physical description and/or quantitative measurements of a wearer's anatomical parts. In some embodiments, the wearer's face may be imaged from the front of the face or the back of the head, for example, from planes that are parallel to the frontal (coronal) plane of the wearer's head. The wearer's face may be imaged from either or both sides of the face, from planes that are parallel to the sagittal plane of the wearer's head. The wearer's face may be imaged from above, in a top view that is parallel to the transverse plane of the wearer's head.

Anatomical structures such as the eyes, nose, ears, eyelashes, and eyebrows may be clearly visible from at least one angle in the digital representation of the wearer. Structures such as the cheekbones (e.g., zygomatic bone and zygomatic arch), browbones (e.g., supraorbital foramen), and bones behind the ears (e.g., mastoid process) may also be imaged and used in lens and frame fitting, for example, as landmarks or as boundaries where an eyewear component may or may not contact. In some embodiments, the digital representation of a user comprises anatomical parts of the wearer. The digital representation may illustrate the morphology (also "form" or "structure") of an anatomical part of the wearer. The digital representation of the wearer may be used by a computing device to construct custom eyewear that start with lens parameters and the digital representation of the wearer, and then determine suitable frame parameters based on the lens parameters and digital representation of the wearer.

Optimizing Lens Parameters

In some aspects as discussed herein, for example to improve optical performance of spectacles (e.g., a frame and mounted lenses therein), a frame may be designed individually (e.g., customized), so that the designed frame keeps ideal (or close to ideal) worn-condition of mounted lenses. In certain embodiments, a computing device may determine lens parameters (e.g., Cornea Vertex Distance (CVD), Pantoscopic Angle (PA) or Face Form Angle (FFA) etc.) for the wearer based on a prescription of the wearer and/or lifestyle parameters (e.g., history of the wearer, activities performed by the wearer, etc.) of the wearer. For example, for progressive addition lenses (PAL), such as common PAL, indoor-use progressive or near vision progressive (incl. "degressive") lenses, lens parameters such as corridor length may be determined by a computing device based on a wearer's life style information. In another example, the basic design of the lens may be determined based on the wearer's lifestyle.

a. In certain aspects, a computing device may receive as input and utilize the prescription data for a wearer of eyewear and lifestyle information of the wearer, to compute lens parameters (e.g., a range of values for lens parameters) for the wearer. In certain embodiments, the computing device may further design custom eyewear for the wearer based on the computed lens parameters and a digital representation of the wearer. For example, below is described an example method performed by a computing device for generating lens parameters for a wearer based on lifestyle information of the wearer. Steps 1-4 include input of prescription and lifestyle information of the wearer into the computing device, and step 5 outputs lens parameters by the computing device. Example of the evaluation method Input Data:

STEP 1: Patient's Prescription

| R | sph +0.25D | cyl −1.25D | Ax 100deg | Add 2.50D |
| L | sph +2.25D | cyl −2.50D | Ax 80deg | Add 2.50D |

STEP 2: Patient's History: Which type of glasses have you mainly used indoors up to now?

| 1 | General Purpose |
| 2 | Reading SV |

| | |
|---|---|
| 3 | Bifocal |
| 4 | Mid-Intermediate PAL |
| 5 | Near Distance Pal (Degressive PAL) |
| 6 | Far Vision SV or common use SV |
| 7 | Naked Eye |

Selection: 4

STEP 3: Basic Indoor Life Style (Importance Level: 0=not important . . . 4=very important), Importance level points: IL(1) to IL(3)

+How important is viewing into far distance (ca 4.5 m) indoors?
  IL(1) 0 . . . 4/Selection: 1
+How important is viewing into intermediate distance (60 cm-1 m) indoors?
  IL(2) 0 . . . 4/Selection: 4
+How important is viewing into near distance (30-50 cm) indoors?
  IL(3) 0 . . . 4/Selection: 4
  Importance level points: IL(4) to IL(6)
+Using computer, which type do you use and how important they are?
  Desktop PC: IL (4) 0 . . . 4/Selection: 3
  Laptop/Notebook: IL(5) 0 . . . 4/Selection: 3
  Pad/Smartphone: IL(6) 0 . . . 4/Selection: 1

STEP 4: Personal Life Style

Select important 5 items. How much important is each of selected item?

(Importance Level: 0=not important . . . 2=very important)

Importance level points: IL (7) to IL(15)

| | |
|---|---|
| +Reading Books or Magazines | IL(7) 0 . . . 2/Selection: 2 |
| +Reading Newspapers | IL(8) 0 . . . 2/Selection: 0 |
| +Watching TV | IL(9) 0 . . . 2/Selection: 2 |
| +Normal Office Work on Desk | IL(10) 0 . . . 2/Selection: 1 |
| +Meeting with several persons | IL(11) 0 . . . 2/Selection: 1 |
| +Playing Music Instruments | IL(12) 0 . . . 2/Selection: 0 |
| +Playing Table Games | IL(13) 0 . . . 2/Selection: 0 |
| +Gardening | IL(14) 0 . . . 2/Selection: 2 |
| +Creative Arts | IL(15) 0 . . . 2/Selection: 0 |

In some aspects, the selection parameters are weighted and related to functional parameters for near, intermediate and far distance zones.

STEP 5: Output of Pantoscopic Angle, Cornea Vertex Distance and Lens Face Form Angle

| | | |
|---|---|---|
| +Ideal PA | Ideal PA for SPACE/SCREEN/CLOSE | Calculated Exp.: 9.0deg |
| +PA max. | Maximum limit value for PA (pant. angle) | Calculated Exp.: 13.0deg |
| +PA min. | Minimum limit value for PA (pant. angle) | Calculated Exp.: 5.0deg |
| +Ideal CVD | Ideal value for Cornea Vertex Distance | Calculated Exp.: 12.1 mm |
| +CVD max. | Maximum limit value for CVD | Calculated Exp.: 13.5 mm |
| +CVD min. | Minimum limit value for CVD | Calculated Exp.: 11.5 mm |
| +Ideal LFFA | Ideal Lens Face Form Angle | Calculated Exp.: 0 deg |
| +LFFA max. | Maximum limit value for LFFA | Calculated Exp.: 9.5deg |
| +LFFA min. | Minimum limit value for LFFA | Calculated Exp.: -2.0deg | b. Calculation of lens parameters and suitable range limits: ideal pantoscopic angle (PA), Ideal Cornea Vertex Distance (CVD), Ideal Lens Face Form Angle (LFFA) and Frame Shape Data In some aspects, ranges of values for lens parameters are calculated as follows by the computing device.

In some aspects, ranges of values for lens parameters are calculated using other suitable calculations.

1) Ideal Pantoscopic Angle (PA): It is defined as the ideal angle in the meridional plane between a horizontal line to the ground and a perpendicular line at the prism reference point on the front surface of a lens, so that a wearer can see into the horizontal direction (primary position) through the fitting point of the lens when the wearer is using a natural head position. In some aspects, the PA may be calculated as follows:

PA1 is an ideal pantoscopic angle, based on the addition of the power right Add(R) and left Add(L) prescription values of the wearer.

The Mean Addition is defined as follows: MAD=(Add(R)+Add(L))/2.

If MAD<2.0 then PA1=8.0.

If MAD>=2.0 then PA1=4/3×(MAD-2)+8.

PAF is an ideal pantoscopic angle of the eyewear mainly used in far distance vision (.e.g., 4 to 5 m).

PAM is an ideal pantoscopic angle of eyewear mainly used in middle distance vision (e.g., 60 cm to 1 m).

PAN an is ideal pantoscopic angle of eyewear mainly used in near distance vision (e.g., 30 to 50 cm).

In an ideal case:
PAF=8.0
PAM=9.0
PAN=10.0

PA2 is an ideal pantoscopic angle based on a wearer's importance level for distance vision PAF, middle distance vision PAM and near distance vision PAN.

In some embodiments, the computing device may select PA2 from PAF, PAM and PAN based on an a most important vision distance for the wearer.

In some embodiments, the computing device may calculate PA2 based on a wearer's lifestyle information (e.g., as input into above mentioned STEP3 and STEP4), by a wearer's importance levels for distance vision, middle distance vision and near distance vision, and/or according to weighting points, as discussed.

In certain embodiments, one or more weighting points and importance levels for indoor progressive lenses may be defined as follows.

The weighting points (WP) of far vision, middle vision and near vision are defined for each life style item.

From STEP 3: Basic Indoor Life Style

Weighting points (1) to (3)

+How important is viewing into far distance (e.g., 4.5 m or more) indoors?

| | Far | Middle | Near |
|---|---|---|---|
| WP(1) | 5 | 0 | 0 |

+How important is viewing into intermediate distance (e.g., 60 cm-1 m) indoors?

|  | Far | Middle | Near |
|---|---|---|---|
| WP(2) | 0 | 5 | 0 |

+How important is viewing into near distance (e.g., 30-50 cm) indoors?

|  | Far | Middle | Near |
|---|---|---|---|
| WP(3) | 0 | 0 | 5 |

+Using computer, which type do you use and how important they are?

| Weighting points (4) to (6) | Far | Middle | Near |
|---|---|---|---|
| WP(4): Desktop PC: | 0 | 8 | 2 |
| WP(5): Laptop/Notebook: | 0 | 3 | 7 |
| WP(6): Pad/Smartphone: | 0 | 3 | 5 |

From STEP 4: Personal Life Style

| Weighting points (7) to (15) | Far | Middle | Near |
|---|---|---|---|
| WP(7): Reading Books or Magazines | 0 | 3 | 7 |
| WP(8): Reading Newspapers | 0 | 5 | 5 |
| WP(9): Watching TV | 8 | 2 | 0 |
| WP(10): Normal Office Work on Desk | 1 | 5 | 4 |
| WP(11): Meeting with several persons | 3 | 2 | 3 |
| WP(12): Playing Music Instruments | 2 | 6 | 2 |
| WP(13): Playing Table Games | 0 | 5 | 5 |
| WP(14): Gardening | 5 | 3 | 2 |
| WP(15): Creative Arts | 1 | 5 | 3 |

Total sum point (TSP) for far vision, middle vision and near vision may be calculated from IL(n) and WP(n), with n=1 . . . 15 as follows.

TSPfar=WPfar(1)×IL(1)+WPfar(2)×IL(2)+ - - - +WPfar(14)×(IL(14)+WPfar(15)×IL(15)

TSPmid=WPmid(1)×IL(1)+WPmid(2)×IL(2)+ - - - +WPmid(14)×(IL(14)+WPmid(15)×IL(15)

TSPnea=WPnea(1)×IL(1)+WPnea(2)×IL(2)+ - - - +WPnea(14)×(IL(14)+WPnear(15)×IL(15)

TSP=TSPfar+TSPmid+TSPnea.

PA2=8×TSPfar/TSP+9×TSPmid/TSP+10×TSPnea/TSP.

The calculated value PA2 for the example above is 9.2. When user's MAD is 2.50 as sample case, PA1 will be 8.7.

The ideal PA is output as ideal pantoscopic angle calculated as follows:

Ideal PA=(PA1+PA2)/2.

In the above mentioned sample case of WP, IL and MAD, Ideal PA will be calculated as follows.

Ideal PA=(PA1+PA2)/2=(8.7+9.2)/2=9.0.

The suitable limits for pantoscopic angle are calculated as follows:

PA max = Ideal PA + 4.0/PA min = Ideal PA − 4.0.

2) Ideal Cornea Vertex Distance (CVD): It is defined as the ideal distance between a wearer's cornea vertex and the back surface of the lens, which is mounted into the frame, on the primary visual direction (horizontal direction).

dMPW is the absolute value of the difference between power components of the right and left lenses as follows:

dMPW=ABSOLUTE((Sph(R)+Cyl(R)/2)−(Sph(L)+Cyl(L)/2))

The ideal corneal vertex distance (Ideal CVD) is calculated as follows.

| if dMPW < 1.0 | then Ideal CVD = 12.5 |
| if 2.0 > dMPW >= 1.0 | then Ideal CVD = (−1)*(dMPW − 1) + 12.5 |
| if dMPW >= 2.0 | then Ideal CVD = 11.5 |

The suitable limits for corneal vertex distance (CVD) are defined as follows.

CVD max=13.5/CVD min=11.5

3) Ideal Lens Face Form Angle (LFFA): It is the ideal angle in the horizontal plane between perpendicular lines on the front surfaces of the right lens and the left lens at each fitting point and the primary position line of sight, crossing the front surfaces of right and left lenses at the fitting points.

The Ideal LFFA is always 0 as ideal condition of frame face form angle because of optical reasons.

LFFA max is the maximum limit as suitable worn condition of frame face form angle.

If a wearer, whose prescription power is high, wears the spectacles with large LFFA value, the wearer tends to feel unnatural or uncomfortable because of inclined images through the right and left lenses, which are inclined horizontally in opposite directions towards the right and left sides. This problem is larger when the horizontal components of the prescription powers of the lenses are high. In the case of weak prescription powers, the problem is smaller.

LFFA max is calculated as follows.

MPWh is defined as the mean power of the right and left horizontal power components as follows.

| MPWh = ((Sph(R) + Cyl(R)*COS(AX(R) + 90))^2 + (Sph(L) + Cyl(L)*COS(AX(L) + 90))^2)/2 | |
| if Absolute(MPWh) < 6.0 | then LFFA max = (−5/6)*Absolute(MPWh) − 6.0) + 5.0 |
| if Absolute(MPWh) >= 6.0 | then LFFA max = 5.0 |

LFFA min is the minimum limit for suitable worn condition. In some aspects, LFFA is limited to zero.

4) Recommended Frame Shape Data: The frame shape data refers to the maximum vertical and horizontal extensions of an eyeglass lens (two-dimensional plane), related to a boxing system (A/B-sizes).

In some aspects, a corridor length can be pre-selected by using a corridor length selection method such as described in US2011/043754(A1), without frame size information and fitting point location on the frame shape.

In some aspects, the corridor length and basic design calculation of progressive design define the minimum, maximum and the ideal distances from the fitting point to upper, lower, right and left edges of assembled lens, and, finally; the ideal lens extensions in horizontal and vertical direction.

For example, in some aspects, the recommended length from fitting point to the upper edge of the frame shape is 12 mm. In some aspects, the minimum length from fitting point to the upper edge of the frame shape is 10 mm.

In some aspects, the recommended length from near fitting point to lower edge of the frame shape is 8 mm. In some aspects, the minimum length from near fitting point to lower edge of the frame shape is 4 mm.

In some aspects, the final corridor length and sums of recommended or minimum lengths from FP to upper edge and from near FP to lower edge will define the recommended (e.g., 20 mm) or the minimum (e.g., 14 mm) vertical frame sizes.

This lens parameter information may be received and used by a computing device to further design custom eyewear for the wearer based on the computed lens parameters and a digital representation of the wearer.

Figure 2:
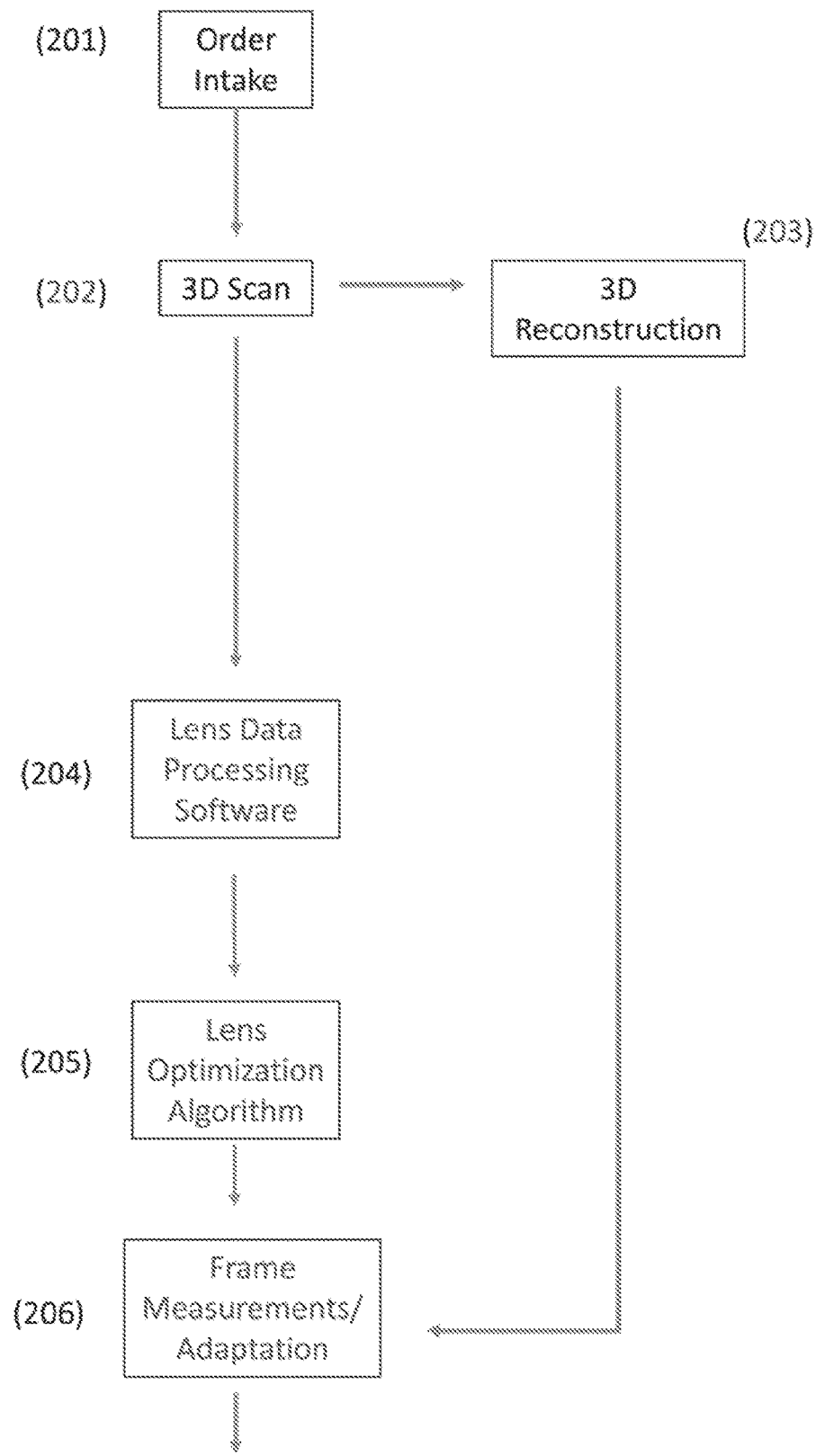
FIG. 2 illustrates example operations for optimizing a lens for a wearer, according to certain aspects.
Figure 3:
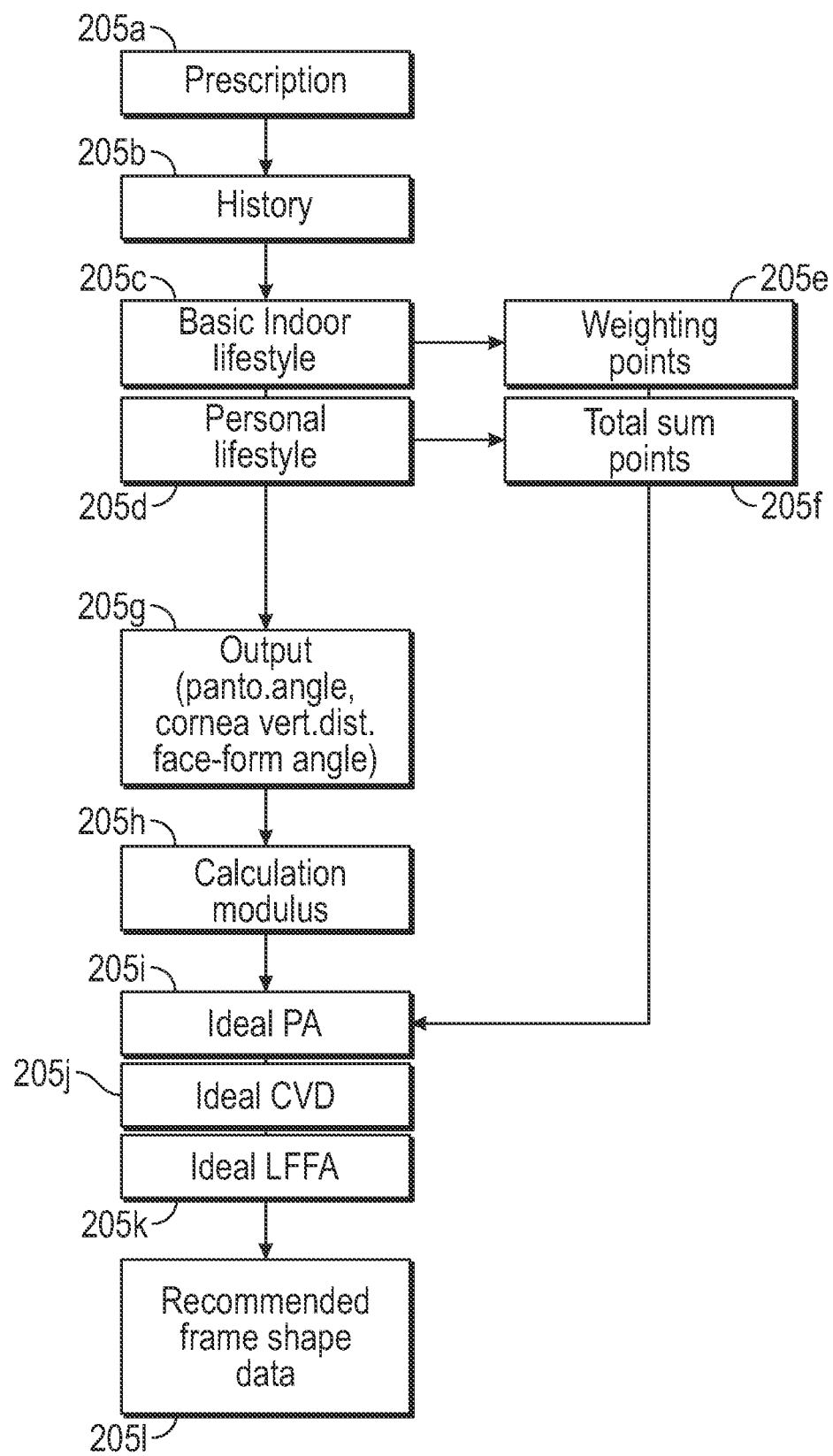
FIG. 3 illustrates example operations for performing a lens optimization method or algorithm of FIG. 2.

FIGS. 2-3 illustrate example operations for optimizing a lens for a wearer. Optionally, at 201, an order is taken in for eyewear for a wearer of lenses. At 202, a computing device receives a 3D scan (e.g., performed by an image capture device) of a wearer for lenses being optimized. Further, at 203, the computing device performs a 3D reconstruction of the 3D scan to generate a digital representation of the wearer (e.g., a digital representation of at least a portion of a head of the wearer). At 204, the computing device receives lens data as an input to lens data processing software. The lens data may include prescription data of the wearer and history of the wearer (e.g., previous eyewear used, previous lens design, etc.). In some aspects, prescription data may comprise measurements for corrective lenses, including measurements for bifocal, trifocal, or multifocal lenses.

The computing device may further receive the lifestyle data (e.g., basic indoor lifestyle and/or personal lifestyle, as discussed herein) of the wearer. As discussed, the lifestyle of the wearer may be an important element when choosing lenses. Wearer information related to the lifestyle of the wearer may therefore comprise information about the type of lenses that the wearer needs, or the activities the wearer will perform with the eyewear. For example, some wearers may use progressive lenses for either indoor or outdoor use and some wearers have occupations or hobbies that involve computer work, reading, and/or other close-up work. In addition, in some aspects, lens type or other lens requirements (e.g., single vision, progressive vision, indoor) information may be received at 204. For example, lens type and other lens requirements may be used by the computing device to determine lens designs that meet the lens type or other lens requirements for the wearer. For example, in some embodiments, lens designs may be selected from progressive lenses, single vision lenses, and work lenses.

At 205, the computing device performs a lens optimization algorithm. For example, the computing device determines one or more lens parameters based on one or more of the lifestyle data of the wearer, lens type or other lens requirements of the wearer, prescription data of the wearer, previous lens design, and history of the wearer. In some aspects, the one or more lens parameters computed by the computing device include one or more of a lens design, a design ID, corridor length, far variation code, near variation code, pantascopic angle (PA) (ideal value plus a range of possible values), corneal vertex distance (CVD) (ideal value plus a range of possible values), lens face form angle (LFFA) (ideal value plus a range of possible values), minimum eye point (Ep) height, minimum B size, and minimum far zone. For example, at 205a, the prescription data of the wearer is input into the lens optimization algorithm. At 205b, the history of the wearer is input into the lens optimization algorithm. At 205c, the basic indoor lifestyle data of the wearer is input into the lens optimization algorithm. At 205d, the personal lifestyle data of the wearer is input into the lens optimization algorithm. At optional 205e, the computing device, uses weighting points to weight the lifestyle data (e.g., based on importance) and at optional 205f sums the weighted lifestyle data to determine one or more lens parameters such as an ideal PA at 205i. Further, based on the inputs, the computing device at 205g computes one or more lens parameters, such as PA, CVD, FFA. etc. At 205h the computing device performs a calculation modulus to compute one or more lens parameters such as ideal PA at 205i, ideal CVD at 205j, and ideal LFFA at 205k. At 205l, the computing device determines a recommended frame shape data based on the lens parameters. At 206, the computing device may determine frame measurements and adaptations for the frames. For example, the computing device may determine one or more of landmarks of the wearer's anatomy and pupillary distance (PD) of the wearer based on the digital representation of the wearer to adapt the frames. In some embodiments, a single sign-on key (SSO) is used. In certain embodiments, 206 may be performed before 205.

In some embodiments, the lens position set by lens parameters places corrective features of the lens in a first region of the lens and places non-essential features in a second region of the lens.

Frame and Lens Fitting

As discussed, lens parameter information may be received and used by a computing device to further design custom eyewear for the wearer based on the computed lens parameters and a digital representation of the wearer.

In certain aspects, for the visual experience of the wearer, some lens parameters may be more important than others. For example, pantascopic angle (PA) and lens face form angle (LFFA) may be set to as close to ideal values as possible or at least within a tolerable range (e.g., a range of tolerated values). In some aspects, when lens are fitted to standard frames in the traditional manner, the ideal PA and LFFA values are difficult to achieve. Consequently, lenses fitted into standard frames often do not have correct PA or LFFA values for the wearer.

As discussed, in contrast to such traditional fitting, the systems and methods described herein may use the correct PA and LFFA values, as well as other lens parameters and wearer anatomy data in order to determine how to fit a frame around lenses that are positioned correctly for the wearer. In some embodiments, lens parameters and wearer anatomy data are used to calculate frame parameters for designing custom eyewear.

Figure 4:
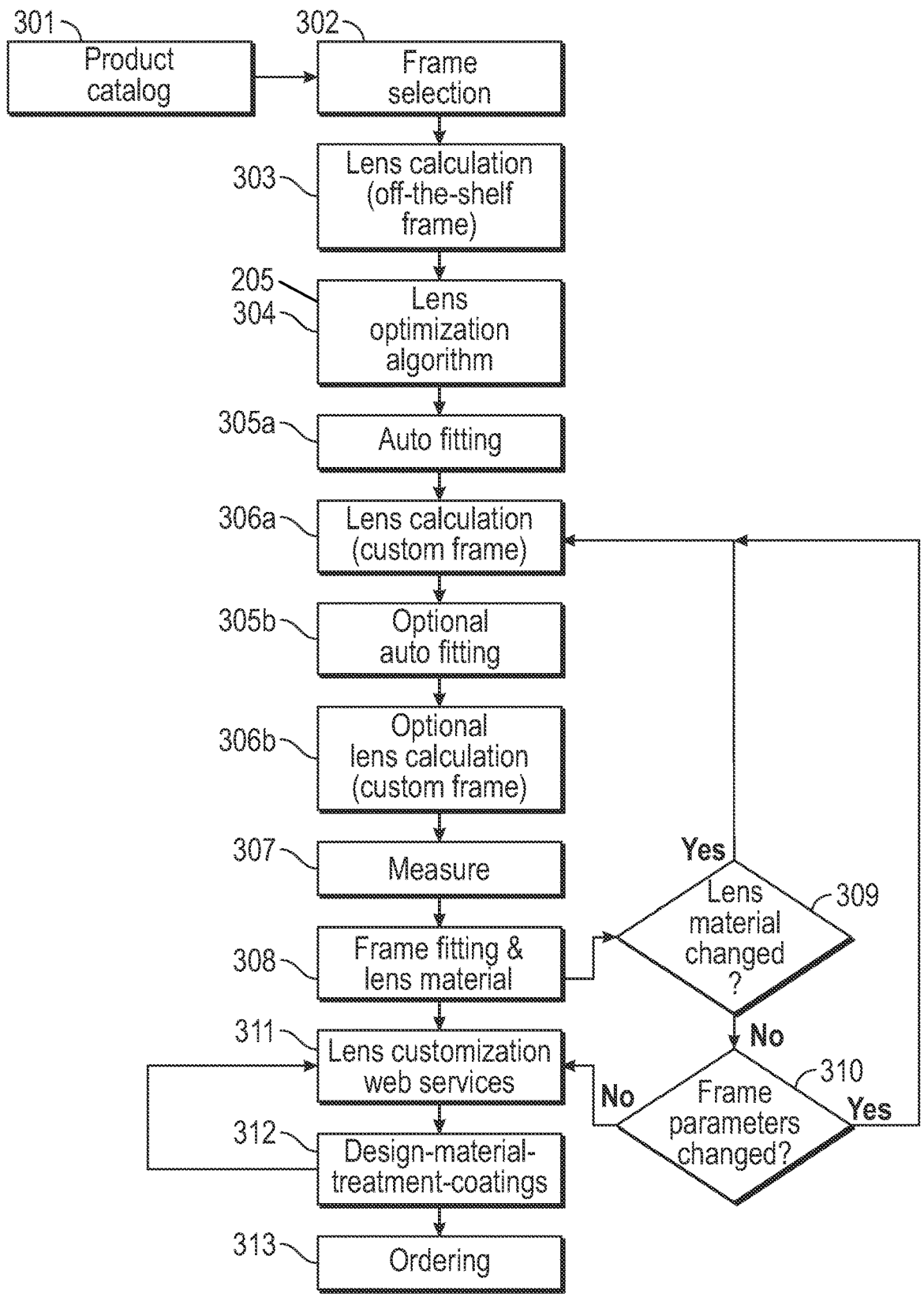
FIG. 4 illustrates example operations for optimizing a lens for a wearer and designing customized eyewear based on the optimized lens, according to certain aspects.

FIG. 4 illustrates example operations for optimizing a lens for a wearer and designing customized eyewear based on the optimized lens, according to certain aspects. At 302, a wearer selects a frame, for example, from a product catalog (301) during frame selection. In certain aspects, the product catalog 301 may be stored on a computing device. In certain aspects, each of the frame designs in the product catalog may have a corresponding set of instructions/parameters for modifying the design of the frame. As an example, a frame designer may specify that the vertical measurement of a frame and the horizontal measurement of the frame should each fall within a range of values in order to be considered an example of the specific design.

The computing device determines frame parameters for the selected frames based on lens parameters for the wearer (calculated as discussed herein). The frame parameters may include one or more of the following: a frame model ID for the selected frame design, distance between lenses (DBL) (defined value and range of acceptable values), Hbox (e.g., horizontal size constraints) (defined value and range of acceptable values), VBox (e.g., vertical size constraints) (defined value and range of acceptable values), inclination (defined value and range of acceptable values), frame face form angle (FFFA) (defined value and range of acceptable values), temple length (defined value and range of acceptable values), parametric model, color options, frame material, groove type, and bevel type.

At 303, in certain embodiments, the computing device perform lens calculations to calculate lens values (e.g., front base curve (BC) for the left and right lenses, back BC for the left and right lenses, CT left, CT right, refraction index (a measure of the lens material), bevel parameters, groove parameters, and any other parameters required for lens ordering). In some embodiments, the computing device may initially calculate lens values for the off-the-shelf frame (e.g., the frame as it is specified in the product catalog according to the initial frame parameters). In some aspects, the computing device uses these calculations as a starting point for adjusting a frame around the lens parameters. The computing device may calculate the lens values based on a combination of measurements comprising one or more of lens code, OMA data (software information), frame material, frame type, bevel type, groove type, prescription data, PD of the wearer (which could also be a measurement representing PD/2), edge thickness, minimal EP height, prism vertical, prism horizontal, and corridor length.

In some embodiments, a lens reconstruction is performed. Using as input one or more of the values of front BC, back BC, CT, and refraction index, a blank lens shape may be created. This is a model based on input parameters.

At 304, in certain embodiments, the computing device performs a lens optimization algorithm, such as lens optimization algorithm 205.

At 305*a*, the computing device auto fits frame parameters to lens parameters. Using one or more parameters related to the lens, frame, and the scanned image of the wearer, the computing device determines how each of the lenses, frame, and wearer's anatomy may be best fitted with each other. Parameters adjusted and optimized by the computing device during this process comprise one or more of a 3D model, landmarks, pantascopic angle (PA) (ideal value plus a range of possible values), corneal vertex distance (CVD) (ideal value plus a range of possible values), lens face form angle (LFFA) (ideal value plus a range of possible values), minimum eye point (Ep) height, minimum B size, minimum far zone, front base curve (BC) for the left and right lenses, back BC for the left and right lenses, CT left, CT right, refraction index, distance between lenses (DBL) (defined value and range of acceptable values), Hbox (defined value and range of acceptable values), VBox (defined value and range of acceptable values), inclination angle (defined value and range of acceptable values), frame face form angle (FFFA) (defined value and range of acceptable values), temple length (defined value and range of acceptable values).

The computing device performs lens calculations on the adjusted, custom frame (306*a*), following the auto-fitting steps. Using a combination of measurements comprising one or more of lens code, OMA data (software information), frame material, frame type, bevel type, groove type, prescription data, PD of the wearer (which could also be a measurement representing PD/2), edge thickness, minimal EP height, prism vertical, prism horizontal, and corridor length, the computing device determines further lens measurements comprising one or more of front base curve (BC) for the left and right lenses, back BC for the left and right lenses, CT left, CT right, refraction index (a measure of the lens material), bevel parameters, groove parameters, and any other parameters required for lens ordering.

In some embodiments, the computing device optionally repeats the auto fitting and lens calculation steps for the custom frame at least once in order to obtain more optimized values for the frame (305*b*) and (306*b*). Auto fitting and lens calculation for the custom frame may be repeated 1, 2, 3, or more times. In certain embodiments, the auto fitting step and lens calculation for the custom frame are not repeated.

The computing device may then measure the fit of the lenses, frames, and the scanned image of the wearer (307).

At 308, the computing device performs a frame fitting for a given lens material, by determining at least one of Hbox (actual and acceptable range), DBL (actual and acceptable range), and temple length (actual and acceptable length). Available lenses to use with such fitted frames may also be indicated, for example, by lens ID.

In some embodiments, a customer changes the lens material (309). In these cases, the computing device performs the lens calculation for the custom frame again (306*a*), optionally repeats the auto fitting and lens calculation for the custom frame (305*b* and 305*b*), measures (307), and performs the frame fitting and lens material step (309) for the new lens material. If the lens material changes again, the steps repeat until the final values for the final lens material are confirmed.

In some embodiments, a customer changes the frame parameters (310). As when the lens material is changed, the computing device performs the lens calculation for the custom frame again (306*a*), optionally repeats the auto fitting and lens calculation for the custom frame (305*b* and 305*b*), measures (307), and performs the frame fitting and lens material step (309). If the frame parameters change again, the steps repeat until the choice is finalized. An exemplary frame material suitable for additive manufacturing is polyamide, which may be available in a flexible, UV resistant, impact resistant, hypo-allergenic and lightweight form.

In certain embodiments, a further step comprises a lens customization web service (311). Taking the input of the lens ID, the computing device performs customization and outputs specifications for a lens customized with coatings, tints, filters, polarization, or photo. A final step of design, material, treatments, and coatings may follow, wherein a customer selects from coatings, tints, filters, polarization, and photo, as well as frame colors, textures, and finishes. The computing device may integrate the selections into a final output describing coating, tint, and finish information for the lenses, and color, texture, and finish information for the frame.

Finally, the customer can check out and order the eyewear having lenses whose position in space has been optimized and whose frames have been fitted around the lenses.

One aspect of the present disclosure is a computer program configured to perform the methods described herein.

Another aspect of the present disclosure is a computer-readable medium comprising computer-executable instructions, which, when executed by a processor, cause the processor to perform the methods described herein.

Customization System

A further aspect of the present disclosure relates to a customization system (FIG. 1) on which a customer, with or without assistance from an eye care professional such as an optician, orders custom eyewear. The customization system performs the methods described herein. In some embodiments, the customization system comprises a scanner unit, a computing device such as a computer wherein the computing device has a processor, memory, a display unit, and input means for entering data related to the customer. The customization system may comprise a user interface for receiving instructions or information from the customer and displaying results. The system may additionally be linked to a network in order to receive or send information from other computers. In some embodiments, the system is configured to send specifications of the eyewear to a manufacturer, for example, the specifications may be sent to a printer for additive manufacturing.

1. Facial Scan

In some embodiments, the scanner unit of the system is configured to make a facial scan of the wearer. In some aspects, the scan accuracy is high. In some embodiments, the scanner unit comprises one or more of a shutter camera and lights. The scanner unit may comprise a flash-power LED for picture rending, and a projection Xenon flash tube for wide angle viewing. In some embodiments, there are 4 industrial grade global-shutter cameras. The cameras may work under both bad light and bright light conditions. In some embodiments, the Xenon flash tubes enable a wider projection angle, so the customer be positioned easily within a short time frame.

The scanner unit may comprise a mirror for fixation, and may comprise an electronic elevator for lifting the scanner unit up and down to accommodate height differences between wearers. For example, the elevator may lift the scanner between 130-190 cm. The elevator may have a power switch and may be controlled by a remote control unit. The scanner unit connects to the computing device via a standard connection such as a USB.

In some embodiments, a customer obtains a facial scan from the scanner unit. In some embodiments, the customer stands upright in front of the scanner unit, at a distance of approximately 1 m, which puts the scanner unit about 2 m from the customer's eyes. In some embodiments, the width of the display is about 25 cm, and the display may be a mirror or mirrored surface. In some embodiments, this mirror width allows the customer to be positioned in the middle of the scanners, while the distance prevents convergence errors. The centered position prevents parallax errors. Accordingly, in some embodiments, it is not necessary to place a mark on ground (such as a line, an x, or a pair of footprints) where the customer needs to stand, since the image of the customer that appears on the screen will indicate the correct position. At this point, an eye care professional can adjust the vertical position of the scanner unit to the correct position in front of the customer's head. After aligning, the eye care professional can take the image and the system continue to complete the process.

In some embodiments, the customization system comprises a display of sample eyewear frames. The display may be a freestanding unit, or may be a display hanging on the wall. The display may shows selection of frames that are suitable for the fitting and optimizing methods described herein, and the customer may touch and try on samples of the designs that (s)he will later select for the fitting. In some embodiments, an entire platform with entire frame collections may be available for display, or may be in the product catalog.

2. Personal Information

The computing device may be configured to receive personal information related to the customer's personal eyewear needs. For example, the customer may enter information, or may have the information imported from other systems which are already linked to the computing device. The customer information comprises details about the customer's visual needs and lifestyle requirements. Near, intermediate, and distance zones may be distributed in the lens as corresponds to the customer's functional needs. The computing device determines the ideal lens design and places the lenses in the position where they will offer the best visual performance and experience.

3. Frame Selection and Customization

In some embodiments, the display unit, which may be a computer screen, shows frames that match the defined position of lenses and still respect anatomical limitations, such as prominent cheekbones or long eyelashes which would form a physical barrier to the lenses. The customer may select a base model (frame selection), with a preferred color and finish. The computing device adjusts automatically for the lenses, for comfort, and for fit on the customer's face.

4. Additional Lens Features

In some embodiments, the customization system enables the customer to select additional lens features for a final lens choice. In some embodiments, an eye care professional helps the customer with this step. The computing device generates a virtual image of the customer in the selected eyewear. In some embodiments, the customer and/or eye care professional can modify the shape of the frame in order to preserve the correct position of the lenses. The modifications may respect the limits that have been predefined, for example, by designers who specify how much the frame components (e.g., temples, nose bridge, frame heights, etc.) can be enlarged or reduced. In some embodiments, the customer may try out different colors or textures in order to configure the frame to his or her personal taste. In some embodiments, the modifications to the frame are also limited by printability.

5. Order and Manufacture

The computing device may be configured to coordinate at least one of ordering, tracking, and manufacturing. The computing device may have software linking the frame and/or lens specifications to one or more manufacturers. In some embodiments, the frame is produced using additive manufacturing. Accordingly, the frame is 3D printed according to the ideal vision and lens parameters and the lenses and precision cut are integrated into the frame. In certain embodiments, the frame and lens are produced by separate manufacturers and assembled. The customer and the eye care professional may follow the progress of the order using track and trace functionality.

6. Delivery to Customer

Following manufacture and assembly of the lenses and frames, the eyewear is delivered to the eye care professional and/or the customer.

Additive Manufacturing

A further aspect of the present invention relates to a customized eyewear product manufactured using the methods described herein. In some embodiments, the custom eyewear is manufactured utilizing conventional 3D printing technology.

Figure 5:
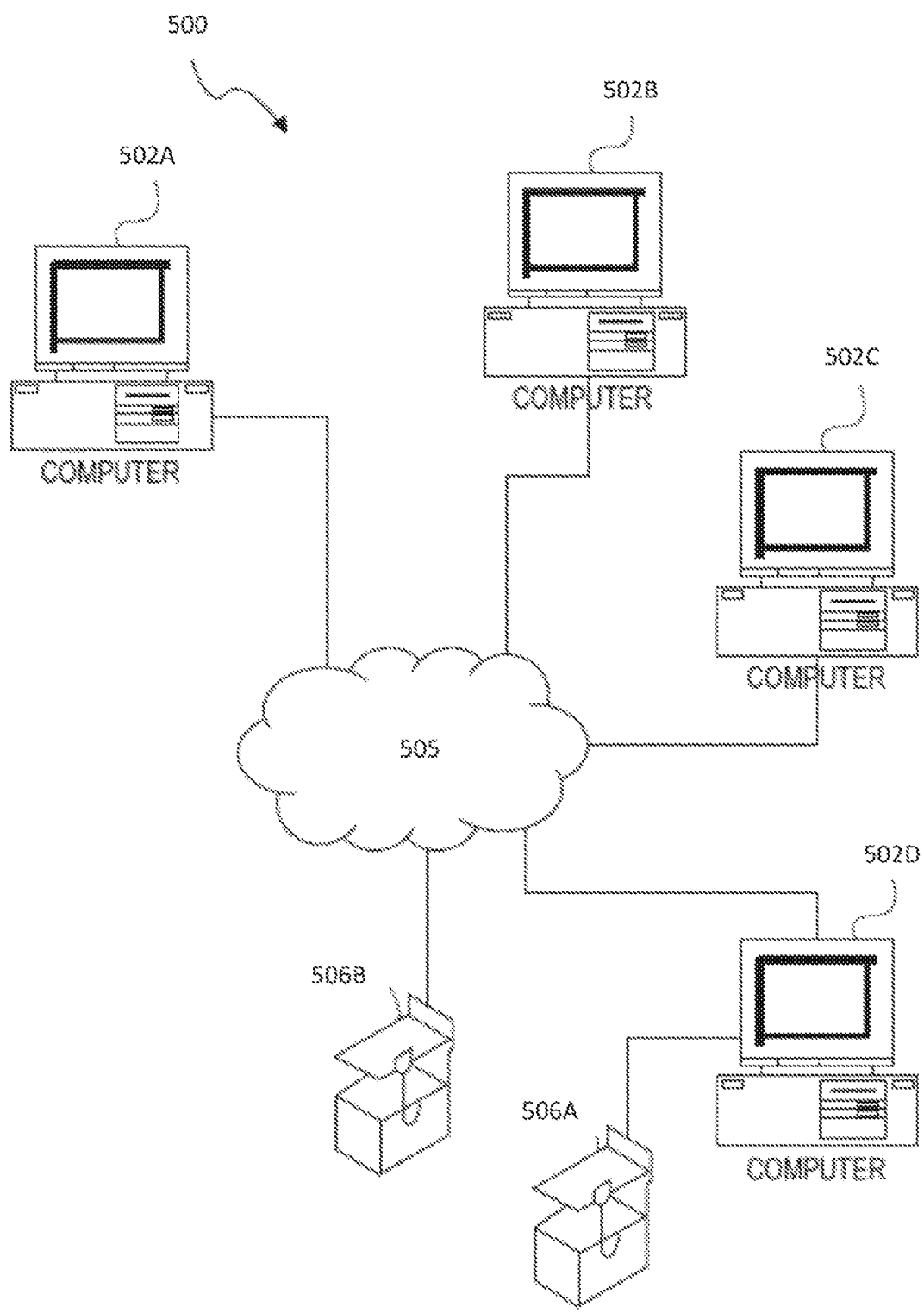
FIG. 5 illustrates one example of a system for designing customized eyewear.

Embodiments of the invention may be practiced within a system for designing and manufacturing 3D objects. Turning to FIG. 5, an example of a computer environment suitable for the implementation of 3D object design and manufacturing is shown. The environment includes a system 500. The system 500 includes one or more computers 502a-502d, which can be, for example, any workstation, server, or other computing device capable of processing information. In some aspects, each of the computers 502a-502d can be connected, by any suitable communications technology (e.g., an internet protocol), to a network 505 (e.g., the Internet). Accordingly, the computers 502a-502d may transmit and receive information (e.g., software, digital representations of 3D objects, commands or instructions to operate an additive manufacturing device, etc.) between each other via the network 505.

The system 500 further includes one or more additive manufacturing devices (e.g., 3D printers) 506a-506b. As shown the additive manufacturing device 506a is directly connected to a computer 502d (and through computer 502d connected to computers 502a-502c via the network 505) and additive manufacturing device 506b is connected to the computers 502a-502d via the network 505. Accordingly, one of skill in the art will understand that an additive manufacturing device 506 may be directly connected to a computer 502, connected to a computer 502 via a network 505, and/or connected to a computer 502 via another computer 502 and the network 505.

It should be noted that though the system 500 is described with respect to a network and one or more computers, the techniques described herein also apply to a single computer 502, which may be directly connected to an additive manufacturing device 506.

Figure 6:
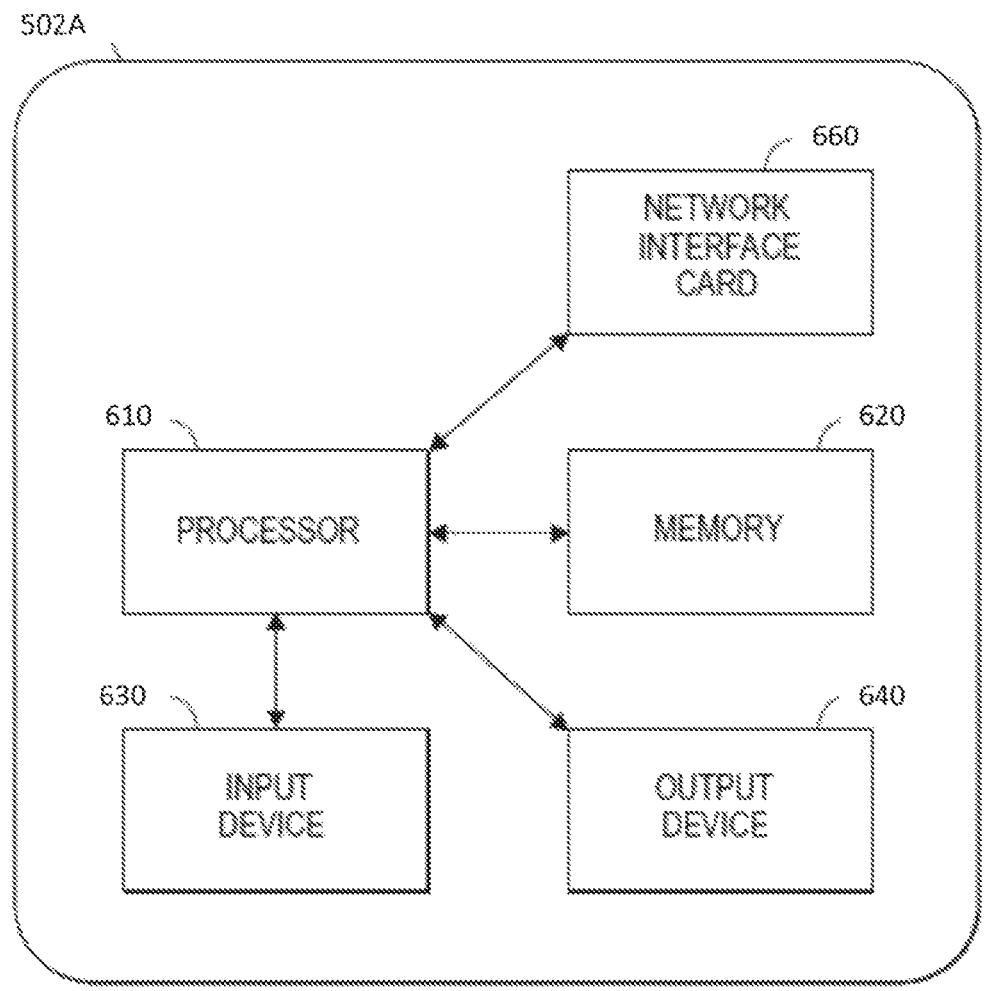
FIG. 6 provides a more detailed view of a computer of the system of FIG. 5.

FIG. 6 illustrates a functional block diagram of one example of a computer of FIG. 5. The computer 502a includes a processor 610 in data communication with a memory 620, an input device 630, and an output device 640. In some embodiments, the processor is further in data communication with an optional network interface card 660. Although described separately, it is to be appreciated that functional blocks described with respect to the computer 502a need not be separate structural elements. For example, the processor 610 and memory 620 may be embodied in a single chip.

The processor 610 can be a general purpose processor, a digital signal processor (DSP), an application specific integrated circuit (ASIC), a field programmable gate array (FPGA) or other programmable logic device, discrete gate or transistor logic, discrete hardware components, or any suitable combination thereof designed to perform the functions described herein. A processor may also be implemented as a combination of computing devices, e.g., a combination of a DSP and a microprocessor, a plurality of microprocessors, one or more microprocessors in conjunction with a DSP core, or any other such configuration.

The processor 610 can be coupled, via one or more buses, to read information from or write information to memory 620. The processor may additionally, or in the alternative, contain memory, such as processor registers. The memory 620 can include processor cache, including a multi-level hierarchical cache in which different levels have different capacities and access speeds. The memory 620 can also include random access memory (RAM), other volatile storage devices, or non-volatile storage devices. The storage can include hard drives, optical discs, such as compact discs (CDs) or digital video discs (DVDs), flash memory, floppy discs, magnetic tape, and Zip drives.

The processor 610 also may be coupled to an input device 630 and an output device 640 for, respectively, receiving input from and providing output to a user of the computer 502a. Suitable input devices include, but are not limited to, a keyboard, buttons, keys, switches, a pointing device, a mouse, a joystick, a remote control, an infrared detector, a bar code reader, a scanner, a video camera (possibly coupled with video processing software to, e.g., detect hand gestures or facial gestures), a motion detector, or a microphone (possibly coupled to audio processing software to, e.g., detect voice commands). Suitable output devices include, but are not limited to, visual output devices, including displays and printers, audio output devices, including speakers, headphones, earphones, and alarms, additive manufacturing devices, and haptic output devices.

The processor 610 further may be coupled to a network interface card 660. The network interface card 660 prepares data generated by the processor 610 for transmission via a network according to one or more data transmission protocols. The network interface card 660 also decodes data received via a network according to one or more data transmission protocols. The network interface card 660 can include a transmitter, receiver, or both. In other embodiments, the transmitter and receiver can be two separate components. The network interface card 660, can be embodied as a general purpose processor, a digital signal processor (DSP), an application specific integrated circuit (ASIC), a field programmable gate array (FPGA) or other programmable logic device, discrete gate or transistor logic, discrete hardware components, or any suitable combination thereof designed to perform the functions described herein.

Figure 7:
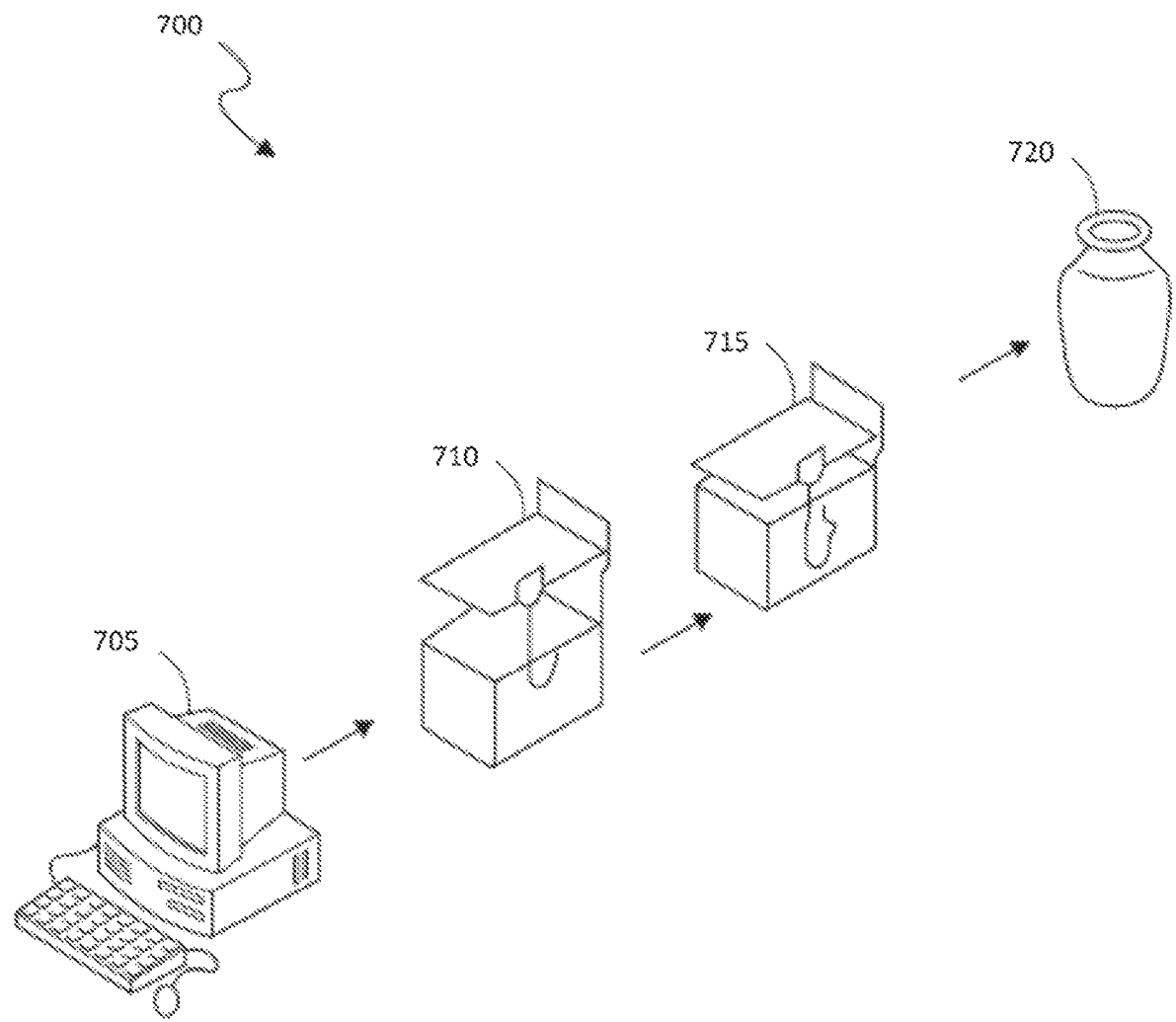
FIG. 7 is an illustration of a general process for manufacturing one or more embodiments of the eyewear frame disclosed herein using an additive manufacturing apparatus of FIG. 5.

FIG. 7 illustrates a process 700 for manufacturing a 3D object or device, such as customized eyewear. As shown, block 705, a digital representation of the object is designed using a computer, such as the computer 502a. For example, 2-D or 3D data may be input to the computer 502a for aiding in designing the digital representation of the 3D object. Continuing block 710, information is sent from the computer 502a to an additive manufacturing device, such as additive manufacturing device 506, and the device 506 commences the manufacturing process in accordance with the received information. The process continues to block 715, where the additive manufacturing device 506 continues manufacturing the 3D object using suitable materials, such as a polymer or metal powder. At block 720, the 3D object is generated.

Figure 8:
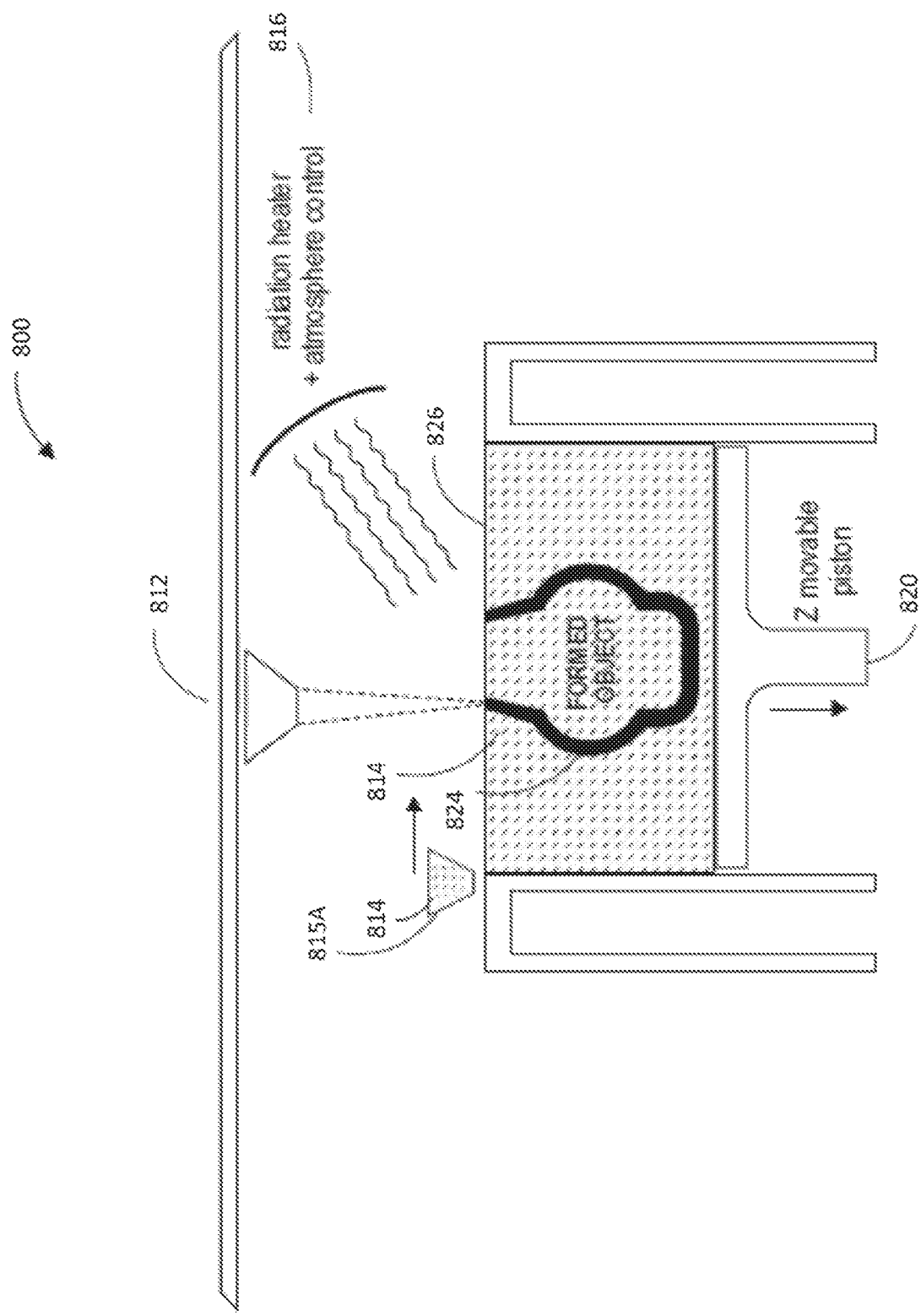
FIG. 8 is an example of an additive manufacturing apparatus that may be used to manufacture eyewear disclosed herein.

FIG. 8 illustrates an exemplary additive manufacturing apparatus 800 for generating a three-dimensional (3D) object. In this example, the additive manufacturing apparatus 800 is a laser sintering device. The laser sintering device 800 may be used to generate one or more 3D objects layer by layer. The laser sintering device 800, for example, may utilize a powder (e.g., metal, polymer, etc.), such as the powder 814, to build an object a layer at a time as part of a build process.

Successive powder layers are spread on top of each other using, for example, a recoating mechanism 815A (e.g., a recoater blade). The recoating mechanism 815A deposits powder for a layer as it moves across the build area, for example in the direction shown, or in the opposite direction if the recoating mechanism 815A is starting from the other side of the build area, such as for another layer of the build.

After deposition, a computer-controlled CO2 laser beam scans the surface and selectively binds together the powder particles of the corresponding cross section of the product. In some embodiments, the laser scanning device 812 is an X-Y moveable infrared laser source. As such, the laser source can be moved along an X axis and along a Y axis in order to direct its beam to a specific location of the top most layer of powder. Alternatively, in some embodiments, the laser scanning device 812 may comprise a laser scanner which receives a laser beam from a stationary laser source, and deflects it over moveable mirrors to direct the beam to a specified location in the working area of the device. During laser exposure, the powder temperature rises above the material (e.g., glass, polymer, metal) transition point after which adjacent particles flow together to create the 3D object. The device 800 may also optionally include a radiation heater (e.g., an infrared lamp) and/or atmosphere control device 816. The radiation heater may be used to preheat the powder between the recoating of a new powder layer and the scanning of that layer. In some embodiments, the radiation heater may be omitted. The atmosphere control device may be used throughout the process to avoid undesired scenarios such as, for example, powder oxidation.

We claim:

1. A computer-implemented method for constructing custom eyewear, comprising:
   receiving wearer information related to anatomy and lifestyle of a wearer of the custom eyewear;
   calculating, based at least in part on the anatomy and lifestyle of the wearer, values for lens parameters, wherein the lens parameters set a lens position that is optimized for the wearer, wherein the lens parameters comprise at least one of lens offset (x & z), pantascopic angle (PA), corneal vertex distance (CVD), lens face form angle (LFFA), minimal eye point height (EPH), minimal B-size, minimal distance to upper, or minimum corridor length;
   obtaining a scanned image showing morphology of an anatomical part of the wearer;
   selecting a frame from a digital catalog; and
   modifying the frame to accommodate the values for the lens parameters and the scanned image, wherein modifying the frame comprises modifying values for one or more frame parameters to accommodate the lens parameters, thereby building the frame and constructing custom eyewear having the lens parameters, wherein the one or more frame parameters comprise one or more of a frame model ID, OMA data, HBox, VBox, incline, frame face form angle (FFFA), parametric model, color options, frame material, groove type, or bevel type.

2. The method of claim 1, wherein the values for the lens parameters are optimized for one or more of prescription data, previous glasses, lens type, or pupillary distance (PD), and the scanned image.

3. The method of claim 2, wherein the prescription data comprises measurements for bifocal, trifocal, or multifocal lenses.

4. The method of claim 1, wherein the lens position set by the lens parameters includes corrective features in a first region of the lens and includes non-essential features in a second region of the lens.

5. The method of claim 1, wherein the values for the lens parameters are selected from an ideal value and a range of tolerated values for the lens parameters.

6. The method of claim 1, wherein selecting the frame comprises choosing a frame that accommodates the values for the lens parameters.

7. The method of claim 1, wherein the one or more frame parameters comprise one or more of the frame model ID, the OMA data, the HBox, the VBox, the incline, the frame face form angle (FFFA), or the parametric model.

8. The method of claim 1, further comprising making a lens calculation based on the one or more frame parameters, wherein the lens calculation approximates the optimal lens for a frame having the frame parameters.

9. The method of claim 8, further comprising performing a lens reconstruction to create 3D lens shape based on the optimal lens from the lens calculation.

10. The method of claim 9, further comprising performing an auto fitting of the 3D lens shape, selected frame, and scanned image showing morphology of an anatomical part of the wearer.

11. The method of claim 10, wherein an output of the auto fitting comprises the lens parameters.

12. The method of claim 11, further comprising adding lens materials or codes to the frame parameters for frame fitting.

13. The method of claim 12, further comprising making a change to a different lens material and performing at least one further iteration of lens calculation, frame optimization, or auto-fitting.

14. The method of claim 12, further comprising making a change to frame parameters and optionally performing at least one further iteration of auto-fitting.

15. The method of claim 13, wherein a final lens calculation is performed based on final calculated lens parameters and frame parameters.

16. The method of claim 15, comprising performing a final check for optimization of lens parameters.

17. The method of claim 12, comprising performing lens customization via a customization web service.

18. The method of claim 17, wherein the lens customization comprises:
   selecting at least one of a frame design, material, treatment, or color;
   selecting at least one of a lens coating, tint, photo, polarization, or filter; and
   ordering the custom eyewear.

19. A computing device comprising:
   a memory; and
   a processor coupled to the memory, the processor being configured to cause the computing device to:
      receive wearer information related to anatomy and lifestyle of a wearer of a custom eyewear;
      calculate, based at least in part on the anatomy and lifestyle of the wearer, values for lens parameters, wherein the lens parameters set a lens position that is optimized for the wearer, wherein the lens parameters comprise at least one of lens offset (x & z), pantascopic angle (PA), corneal vertex distance (CVD), lens face form angle (LFFA), minimal eye point height (EPH), minimal B-size, minimal distance to upper, or minimum corridor length;
      obtain a scanned image showing morphology of an anatomical part of the wearer;
      select a frame from a digital catalog; and
      modify the frame to accommodate the values for the lens parameters and the scanned image, wherein modifying the frame comprises modifying values for one or more frame parameters to accommodate the lens parameters, thereby building the frame and constructing custom eyewear having the lens parameters, wherein the one or more frame parameters comprise one or more of a frame model ID, OMA data, HBox, VBox, incline, frame face form angle (FFFA), parametric model, color options, frame material, groove type, or bevel type.

20. A non-transitory computer-readable medium comprising computer-executable instructions, which, when executed by a processor, cause the processor to perform a method comprising:
   receiving wearer information related to anatomy and lifestyle of a wearer of a custom eyewear;
   calculating, based at least in part on the anatomy and lifestyle of the wearer, values for lens parameters, wherein the lens parameters set a lens position that is optimized for the wearer, wherein the lens parameters comprise at least one of lens offset (x & z), pantascopic angle (PA), corneal vertex distance (CVD), lens face form angle (LFFA), minimal eye point height (EPH), minimal B-size, minimal distance to upper, or minimum corridor length;

obtaining a scanned image showing morphology of an anatomical part of the wearer;

selecting a frame from a digital catalog; and modifying the frame to accommodate the values for the lens parameters and the scanned image, wherein modifying the frame comprises modifying values for one or more frame parameters to accommodate the lens parameters, thereby building the frame and constructing custom eyewear having the lens parameters, wherein the one or more frame parameters comprise one or more of a frame model ID, OMA data, HBox, VBox, incline, frame face form angle (FFFA), parametric model, color options, frame material, groove type, or bevel type.

* * * * *